(12) United States Patent
Valencia

(10) Patent No.: US 6,190,333 B1
(45) Date of Patent: Feb. 20, 2001

(54) THREADER DEVICE FOR THREADING A GUIDEWIRE INTO A CATHETER

(75) Inventor: Carlos A. Valencia, Hialeah, FL (US)

(73) Assignee: Mark II Research and Development Corp., Miami, FL (US)

( * ) Notice: Under 35 U.S.C. 154(b), the term of this patent shall be extended for 0 days.

(21) Appl. No.: 09/419,181

(22) Filed: Oct. 15, 1999

(51) Int. Cl.[7] .................................................. A61B 5/00
(52) U.S. Cl. ............................................................ 600/585
(58) Field of Search ................................... 600/585, 434, 600/435; 604/160, 166, 171

(56) References Cited

U.S. PATENT DOCUMENTS

| | | | |
|---|---|---|---|
| 4,799,496 | 1/1989 | Hargreaves et al. | 128/772 |
| 4,907,332 | * 3/1990 | Christain et al. | 600/434 |
| 4,917,094 | 4/1990 | Lynch et al. | 128/657 |
| 5,045,061 | 9/1991 | Seifert et al. | 604/96 |
| 5,191,888 | * 3/1993 | Palmer et al. | 600/585 |
| 5,234,002 | 8/1993 | Chan | 128/772 |
| 5,234,407 | 8/1993 | Tierstein | 604/53 |
| 5,246,009 | 9/1993 | Adams | 128/772 |
| 5,255,690 | 10/1993 | Keith | 128/772 |
| 5,325,746 | 7/1994 | Anderson | 81/487 |
| 5,325,868 | 7/1994 | Kimmelstiel | 128/772 |
| 5,358,495 | 10/1994 | Lynn | 604/171 |
| 5,361,777 | 11/1994 | Sellers | 128/772 |
| 5,377,683 | 1/1995 | Ueno et al. | 128/660.1 |
| 5,392,778 | 2/1995 | Horzewski | 128/657 |
| 5,464,023 | 11/1995 | Viera | 128/772 |
| 5,634,475 | 6/1997 | Wolvek | 128/772 |
| 5,830,157 | * 11/1998 | Foote | 600/585 |
| 6,106,487 | * 8/2000 | Duane et al. | 600/585 |

FOREIGN PATENT DOCUMENTS

0328760 A2   12/1988   (EP) .

* cited by examiner

*Primary Examiner*—Max Hindenburg
(74) *Attorney, Agent, or Firm*—David P. Gordon; David S. Jacobson; Thomas A Gallagher

(57) ABSTRACT

A threader device includes two substantially symmetrical elongate body members each having an inner face provided with a channel, an aligning guide, a first end, a second end, a hinge portion, and a locking portion. The two body members are pivotally coupled together at the hinge portions. When the two body members are in a closed position, the channels of the two body members together define a longitudinal passage having a stepped cylindrical cavity and a funnel at each of the first and second ends. The cavity is adapted to receive the distal end of a balloon catheter. Additionally, the cavity may receive and securely hold a non-balloon type catheter. One funnel is adapted to direct a guidewire into the cavity. The locking portions are adapted to create a snap closure for the threader device.

20 Claims, 3 Drawing Sheets

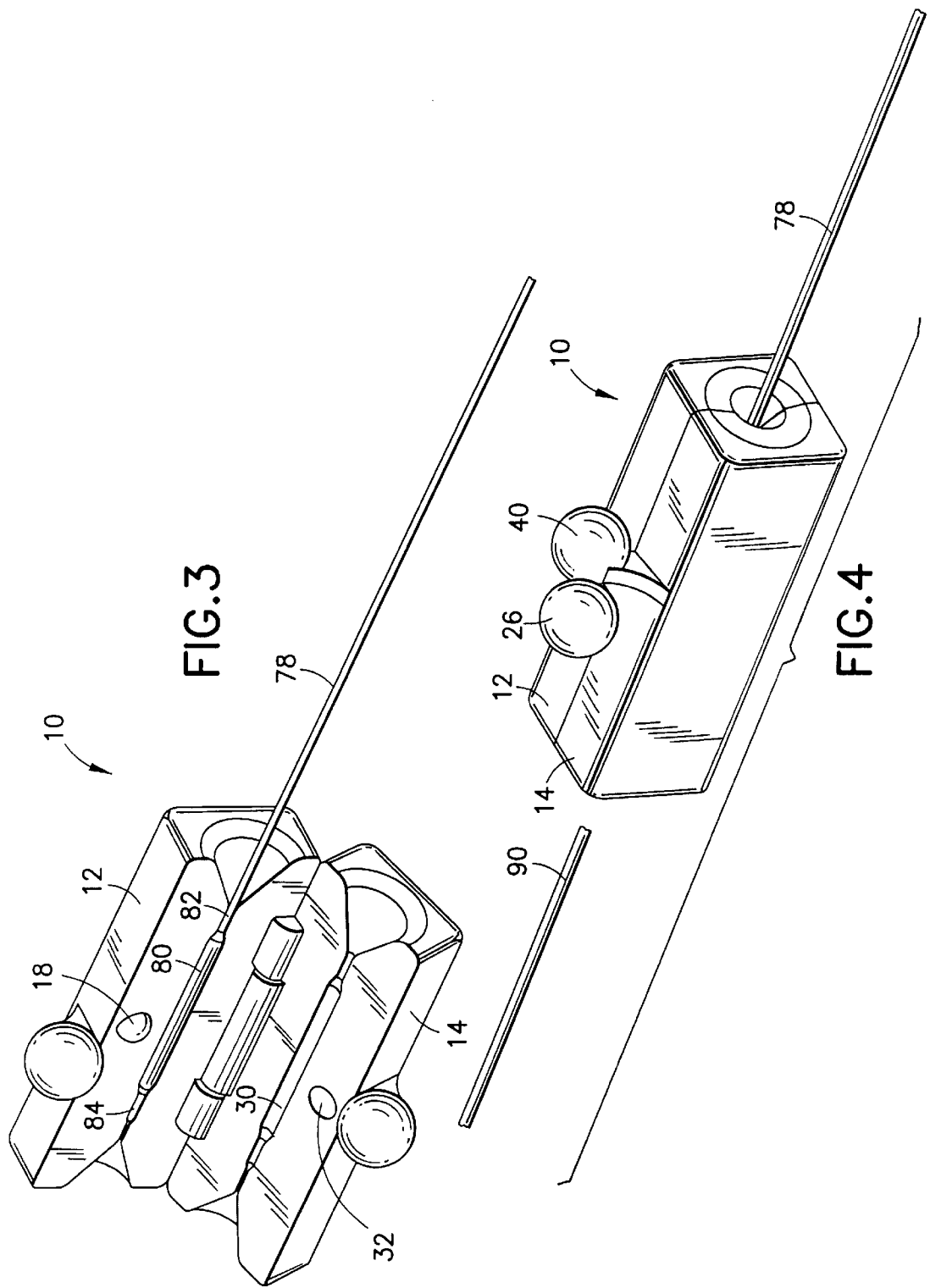

THREADER DEVICE FOR THREADING A GUIDEWIRE INTO A CATHETER

BACKGROUND OF THE INVENTION

1. Field of the Invention

This invention relates broadly to surgical devices. More particularly, this invention relates to devices for assisting the insertion of a guidewire into a catheter.

2. State of the Art

Catheterization procedures are well known for diagnosis and therapy of lesions in the cardiovascular system. One such procedure is angioplasty, for eliminating or ameliorating the vascular blockage or constriction in blood vessels associated with supplying blood to the heart or other organs. In an angioplasty procedure, an expandable balloon carried by an elongated catheter is introduced into the arterial system of a patient and advanced until it is positioned in the region of the blockage or constriction. Once so positioned, the balloon is expanded by filling it with a fluid. In successful procedures, the expandable balloon presses outwardly against the walls of the artery and expands the artery to a degree to which the artery is either partially or completely reopened to blood flow.

Prior to initiating the angioplasty procedure, a guiding catheter is placed, typically via the femoral artery, into the aorta and its tip is engaged into the coronary arteries which branch from the aorta. Once placed, the guiding catheter acts as a conduit to access the coronary arteries with a guidewire and balloon catheter. The guiding catheter is a portion of plastic tubing having a length of about 95 centimeters, an inside diameter of about 2 millimeters, and an outside diameter of about 2.5 millimeters. A hemovalve, i.e., a valve preventing blood loss through the guiding catheter when a tubular conduit such as a balloon catheter is passed therethrough, is provided at the proximal end of the guiding catheter.

Then, external of the patient, the physician threads a guidewire through a balloon catheter for subsequent insertion through the guiding catheter to the location of the lesion for balloon dilation of the lesion. The guidewire is a metal wire, e.g., titanium or nickel-titanium alloy wire, approximately 175 centimeters in length, and about 0.25 to 0.46 millimeters in diameter. The balloon catheter is an elongate flexible plastic tubular member defining two longitudinal passages and having the balloon located at or adjacent its distal end. One longitudinal passageway defines a conduit through which the guidewire can be passed. The other longitudinal passage defines a conduit in fluid communication with the interior of the balloon and through which inflation fluid can be injected to inflate the balloon. The proximal end of the guidewire is thread into the distal end of the catheter, permitting insertion of the distal end of the guidewire into the patient and subsequent sliding of the distal end of the catheter over the guidewire to position an expandable balloon at the site of the lesion.

While the procedure has been quite effective, the process of threading the guidewire through the balloon catheter remains a frustrating and time consuming task. The guidewire and balloon catheter are both very small in diameter and relatively long, and it is difficult for the physician to hold one in each hand in a manner which facilitates threading the proximal end of the guidewire into the small opening of the distal end of the balloon catheter. In addition, the delicate balloon can be easily and unintentionally damaged by the manipulation required for the threading procedure.

Publication EP 0328760 A2 describes a threader device intended to assist the threading of a guidewire into a catheter. The threader device includes two semi-cylindrical halves each having portions of threads on their exterior surfaces such that when the halves are positioned together to form a cylinder, the exterior surfaces of the two halves together define complete external helical threads. A removable threaded collar is positioned over the external threads and holds the halves together. The two halves together define a passage having a cylindrical central portion and two funnel-shaped end portions. The funnel at a first end portion is sized to readily receive an end of the catheter, while the funnel at the second end portion has a larger end adapted to readily receive the guidewire and a tapered end sized smaller than the outer diameter of the catheter yet sufficiently large to receive an end of the guidewire.

In use, the catheter is pushed into the funnel at the first end portion, through the central portion, and butt against the funnel at the second end portion. The guidewire is then inserted through the funnel of the second end portion where it is directed into the catheter, and a sufficient length of guidewire is fed therein.

However, the device of publication EP 0328760 A2 has several significant drawbacks. First, after the guidewire is threaded into the catheter, the threader device must be removed from over the catheter to permit the distal end of the catheter to enter the guiding catheter and the human body. However, it is difficult to remove the threader device from over the catheter and the guidewire after the guidewire has been threaded into the catheter. While the collar can be removed from over the halves to free the halves from the catheter and guidewire, the collar is still trapped over the catheter and guidewire. The only way to remove the collar is to slide the collar over the relatively long length of either the catheter or the guidewire. This requires complete uncoiling of one of the otherwise neatly coiled catheter and guidewire. Otherwise, the collar must be obtrusively left thereover. Second, the unassembled device includes three separate and distinct elements, two halves and a collar, any of which may become misplaced or lost. Third, the passageway of the threader device is not particularly adapted to receive the balloon at the distal end of a balloon catheter, as the cylindrical passage in the device is configured only for use with non-balloon catheters. Fourth, even if a balloon is forced into the passageway, the passageway is apparently not of sufficient length to surround a balloon over the entire length of the balloon. As such, a portion of the balloon may extend external of the threader device and potentially be subject to inadvertent damage.

SUMMARY OF THE INVENTION

It is therefore an object of the invention to provide a threader device for threading a guidewire into a catheter.

It is another object of the invention to provide a threader device which can easily be applied over and removed from a catheter or guidewire.

It is a further object of the invention to provide a threader device which has relatively few discrete elements, and preferably which is assembled into a single structure.

It is an additional object of the invention to provide a threader device adapted to securely and protectively hold a balloon catheter during the threading procedure.

It is also an object of the invention to provide a threader device which can be used to protect the balloon of a balloon catheter during shipping and storage.

In accord with these objects, which will be discussed in detail below, a threader device is provided which includes two substantially symmetrical elongate body members each having an inner face provided with a channel, an aligning guide, a first end and a second end, and a hinge. The two body members are pivotally coupled together at the hinge. When the two body members are in a closed position, i.e., pivoted about the hinge such that their inner faces are substantially in contact and their channels are substantially aligned, the channels of the two body members together define a longitudinal passage having a central preferably stepped cylindrical cavity and a funnel at each of the first and second ends. The cavity is adapted to receive a balloon of a balloon catheter and the distal end of the catheter which typically extends beyond the balloon. Additionally, the cavity may receive and securely hold a non-balloon type catheter. The funnel at the first end provides a smooth curve to prevent kinking of a catheter positioned in the cavity, while the funnel at the second end is adapted in size to readily receive the guidewire and guide the guidewire into a balloon catheter or other catheter positioned therein. At least one body member also includes a locking element which secures the threader device in a closed position. The locking element is preferably integrally molded with a body member of the threader device and permits the threader device to be rapidly secured over and rapidly released from any portion of a catheter and guidewire without necessitating sliding any portion of the threader device over a length of one of the catheter and the guidewire.

In a preferable use, after manufacture of a balloon catheter, the distal end of a balloon catheter is provided into the channel of one of the body members and the body members are closed and secured about the balloon catheter. The threader device provides a protective package for the balloon on the catheter. Then, at the required time during an angioplasty procedure, an end of a guidewire can be fed through the funnel at the second end of the threader and guided into the catheter. The threader device can then be unlocked and easily removed from over the threaded catheter and guidewire.

Additional objects and advantages of the invention will become apparent to those skilled in the art upon reference to the detailed description taken in conjunction with the provided figures.

BRIEF DESCRIPTION OF THE DRAWINGS

FIG. 3 is a perspective view of the threader device according to the invention shown in an open position and provided with a catheter; and FIG. 4 is a perspective view of the threader device according to the invention shown in a closed position.

DETAILED DESCRIPTION OF THE PREFERRED EMBODIMENTS

Figure 1:
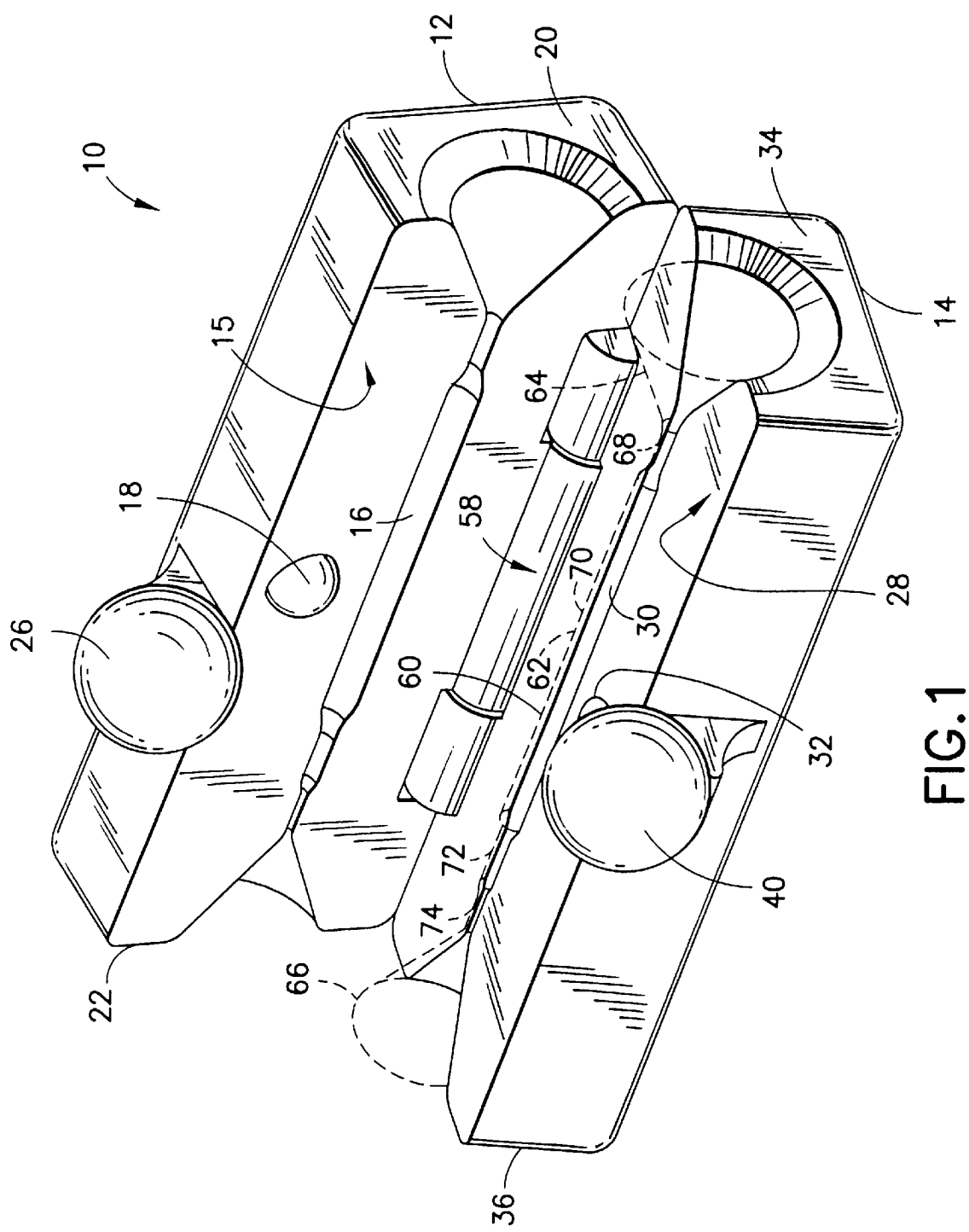
FIG. 1 is a perspective view of the threader device according to the invention shown in an open position.
Figure 2:
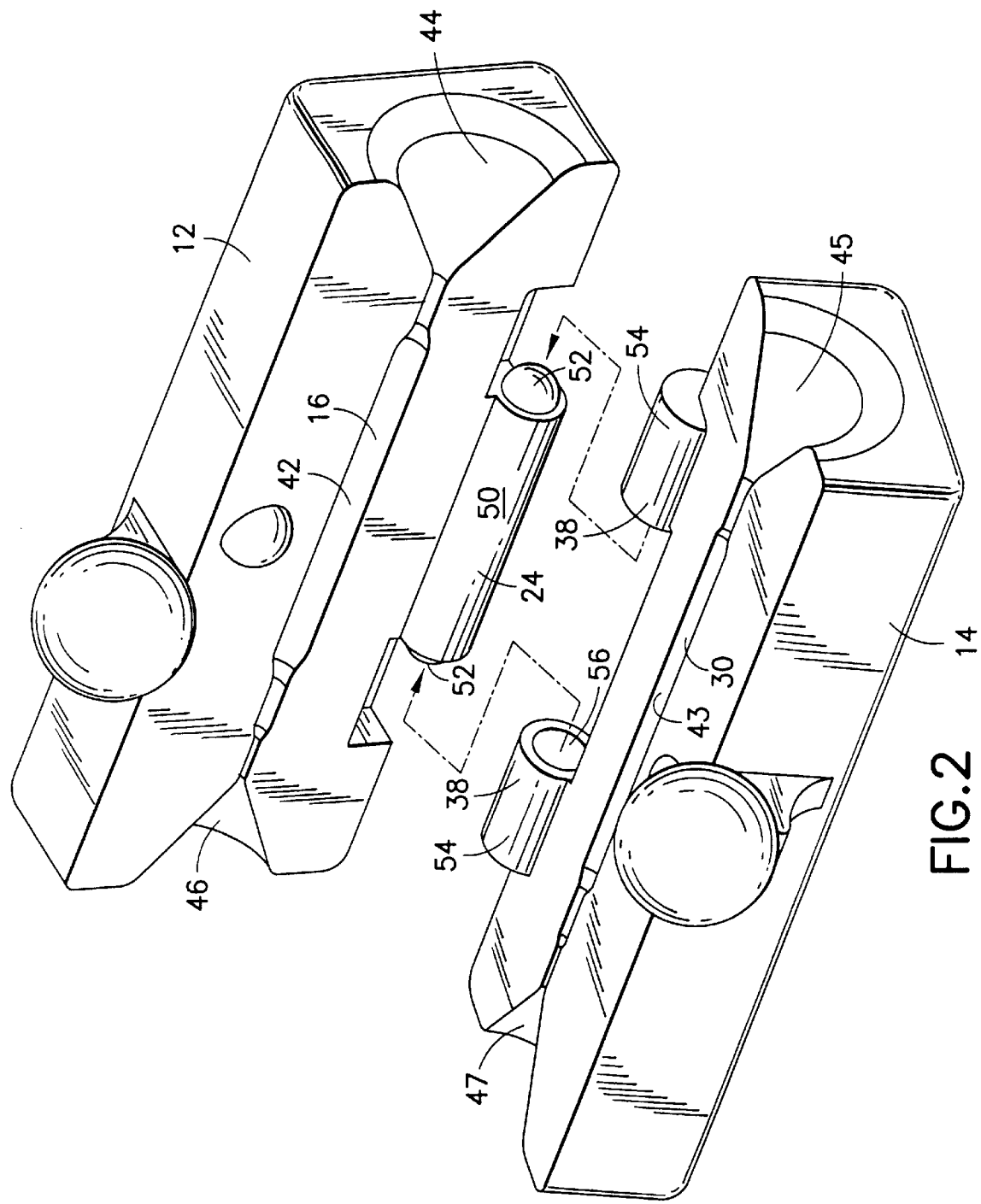
FIG. 2 is an exploded perspective view of the threader device according to the invention.

Turning now to FIGS. 1 and 2, a threader device 10 according to the invention is shown. The threader device 10 includes first and second substantially symmetrical elongate body members 12, 14. The first body member 12 is preferably molded to include an inner face 15 provided with a channel 16, a male aligning guide 18, a first end 20, a second end 22, a hinge portion 24, and a locking portion 26. The second body member 14 is preferably molded to also include an inner face 28 provided with a channel 30, a female aligning guide 32 (see FIG. 3), a first end 34, a second end 36, a hinge portion 38, and a locking portion 40. The channels 16, 30 of each body member 12, 14 includes a preferably stepped central portion 42, 43 and flared end portions 44, 45 and 46, 47.

The hinge portion 24 of body member 12 includes a central element 50 having preferably hemispherical male pins or protuberances 52, and the hinge element 38 of body member 14 includes lateral elements 54 each having medially directed female receptacles 56 for the pins 52. The central element 50 may be forced between the lateral elements 54 to form a hinge 58 about which the two body members 12, 14 may be relatively pivoted between open and closed positions and which permits the inner surfaces 15, 28 of the two body members to flushly seat against one another when in the closed position.

When moving the two body members into a closed position, the aligning guides 18, 32 mate and ensure that the channels 16, 30 of each body members are substantially aligned such that the channels define a longitudinal passage 60 in the closed threader device (shown in dotted lines in the open threader device of FIG. 1). The longitudinal passage 60 has a preferably stepped central cylindrical cavity 62 and a funnel 64, 66 at each of the first and second ends. The stepped cylindrical cavity 62 preferably includes a proximal catheter receiving portion 68 (having a diameter of approximately 0.50 mm–4.00 mm) adjacent the funnel 64 at the first end, a central balloon receiving portion 70 (having a diameter of approximately 1.00 mm–4.00 mm), a relatively distal balloon tip receiving portion 72 (having a diameter of approximately 0.50 mm–4.00 mm), and a distal guidewire receiving portion 74 (having a diameter of approximately 0.35–0.90 mm) adjacent the funnel 66 at the second end. The distal guidewire receiving portion 74 preferably has a diameter smaller than the outer diameter of a catheter and a balloon tip.

Turning now to FIGS. 1 and 3, due to the stepped nature of the channels 16, 30, and the resulting cavity 62, the channels and cavity are particularly adapted to receive the distal end of a balloon catheter 78. The balloon 80 is receivable in the balloon receiving portion 70, the catheter 82 proximal the balloon is receivable in the catheter receiving portion 68, and the balloon tip 84 (a portion of the catheter 82 extending distal of the balloon 80) is receivable in the balloon tip receiving portion 72. Additionally, the stepped cavity 62 may receive and securely hold a non-balloon type catheter with the distal portion of the catheter held in the catheter receiving portion 68 and the balloon tip receiving portion 72.

Referring now to FIG. 4, the locking portion 26, 40 of each body member 12, 14 of the threader device 10 is preferably adapted to snap with the locking portion of the other body member in a snap closure and thereby secure the threader device 10 in the closed position about the balloon catheter 78. The locking portions 26, 40 can be unsnapped to permit the threader device to enter an open position (FIG. 1) and release a balloon catheter held therein.

In a preferred use, the distal end of a balloon catheter is provided into the channel of one of the body members, as described above, and the body members 12, 14 are closed and locked together with the locking elements 26, 40, about the balloon catheter. The threader device 10 thereby provides a protective package for the balloon on the catheter, as shown, which remains over the balloon catheter until the balloon catheter is needed for use. The funnel 64 provides a smoothly curving surface which prevents kinking of the catheter positioned in the cavity 62. Alternatively, the balloon catheter may be provided separate from the threader device and provided into the threader device at the time of the angioplasty procedure.

Then, and referring now to FIGS. 1 and 4, at the required moment during the angioplasty procedure, the proximal end of a guidewire 90 can be fed through the funnel 66 at the first end of the threader device, guided into the guidewire portion 74 of the cavity 62, and aligned for insertion into the balloon tip 84 of the catheter 78. A sufficient length of the guidewire 90 can then be rapidly fed into the catheter 78. The threader device 10 can then be unlocked and easily removed from over catheter and guidewire. Removal can be performed without necessitating sliding any portion of the threader device 10 over a length of one of the catheter or the guidewire.

Additionally, according to a second use of the invention, the threader device 10 may be used with a catheter which does not include a balloon at its distal end. In this use, the threader device is preferably provided in a closed and locked configuration. The distal end of the catheter is then guided by the funnel 64 at the first end into the cavity 62 such that a distal length of the catheter extends in both the catheter receiving portion 68 and the balloon tip receiving portion 72 to abut the guidewire receiving portion 74. A guidewire may then be guided by the funnel 66 into the guidewire receiving portion 74 and further into the catheter.

There have been described and illustrated herein embodiments of a threader device and a method of threading a guidewire into a catheter. While particular embodiments of the invention have been described, it is not intended that the invention be limited thereto, as it is intended that the invention be as broad in scope as the art will allow and that the specification be read likewise. Thus, while particular aligning guides have been disclosed, it will be appreciated that other aligning guides may be used as well. Furthermore, while a particular hinge has been disclosed it will be appreciated that another hinge can be used to pivotally couple the two members of the threader device together. For example, a hinge integrally molded with the two body members may be used. In addition, while a two element snap lock is disclosed, it will be appreciated that other closures may be provided. For example, the closure may include a single locking element on one of the body members which is adapted to lock with the other body member. Moreover, the one or more locking elements may lock by a mechanism other than a snap fit, e.g., a latch, a barbed catch, a friction fit, a tie, a U-shaped band, or other mechanism which hold the threader device closed, while permitting the threader device to be removed from over the catheter and guidewire without sliding along a length thereof. It will therefore be appreciated by those skilled in the art that yet other modifications could be made to the provided invention without deviating from its spirit and scope as so claimed.

What is claimed is:

1. A threader device for guiding a guidewire into a catheter, comprising:
   a) a first body member having a first hinge portion and a first inner face provided with a first channel having a flared end; and
   b) a second body member having a second hinge portion pivotally coupled to said first hinge portion, and a second inner face provided with a second channel having a flared end,
      wherein when said first body member is rotated relative to said second body member about said second hinge such that said first inner face is substantially in contact with said second inner face, said first and second channels define a cavity adapted to receive and hold the catheter, and said flared ends define a funnel for guiding the guidewire into the catheter.

2. A threader device according to claim 1, wherein: said cavity is stepped in diameter.

3. A threader device according to claim 2, wherein: said cavity includes a first end portion, a second end portion, and a central portion between said first and second end portions, said central portion being relatively larger in diameter than said first and second end portions.

4. A threader device according to claim 3, wherein: said second end portion of said cavity includes a first section sized to receive a portion of the catheter and a relatively smaller section sized to receive the guidewire.

5. A threader device according to claim 1, wherein: said threader device includes an aligning means for facilitating alignment of said first and second channels of said first and second body members.

6. A threader device according to claim 1, wherein: said threader device includes a locking means for locking said first and second body members in a closed position in which said first and second channels form said cavity.

7. A threader device according to claim 6, wherein: said locking means is integrally molded with at least one of said first and second body members.

8. A threader device according to claim 6, wherein: said locking means includes a first locking member on said first body member, and a second locking member on said second body member, said first and second locking members positioned to snap together in a snap fit engagement.

9. A threader device for guiding a guidewire into a catheter, comprising:
   a) a first body member having a first inner face provided with a first channel having a flared end;
   b) a second body member having a second inner face provided with a second channel having a flared end; and
   c) means for coupling said first body member to said second body member,
      wherein when said first body member is coupled to said second body member such that said first inner face is substantially in contact with said second inner face, said first and second channels define a stepped cavity adapted to receive and hold the catheter, and said flared ends define a funnel for guiding the guidewire into the catheter.

10. A threader device according to claim 9, wherein: said cavity includes a first end portion, a second end portion, and a central portion between said first and second end portions, said central portion being relatively larger in diameter than said first and second end portions.

11. A threader device according to claim 10, wherein: said second end portion of said cavity includes a first section sized to receive a portion of the catheter and a relatively smaller section sized to receive the guidewire.

12. A threader device according to claim 9, wherein: said threader device includes an aligning means for facilitating alignment of said first and second channels of said first and second body members.

13. A threader device according to claim 9, wherein:

said threader device includes a locking means for locking said first and second body members in a closed position in which said first and second channels form said cavity.

14. A threader device according to claim 13, wherein:

said locking means is integrally molded with at least one of said first and second body members.

15. A threader device according to claim 13, wherein:

said locking means includes a first locking member on said first body member, and a second locking member on said second body member, said first and second locking members positioned to snap together in a snap fit engagement.

16. A threader device for guiding a guidewire into a catheter, comprising:

a) a first body member having a first channel having a flared end;

b) a second body member having a second channel having a flared end;

c) a hinge element coupling said first and second body members together such that said first body member is rotatable relative to said second body member, wherein when said first body member is rotated relative to said second body member about said hinge element such that said first channel is aligned with said second channel, said first and second channels define a cavity adapted to receive and hold the catheter, and said flared ends define a funnel for guiding the guidewire into the catheter.

17. A threader device according to claim 16 wherein:

said cavity is stepped in diameter.

18. A threader device according to claim 17, wherein:

said cavity includes a first end portion, a second end portion, and a central portion between said first and second end portions, said central portion being relatively larger in diameter than said first and second end portions.

19. A threader device according to claim 18, wherein:

said second end portion of said cavity includes a first section sized to receive a portion of the catheter and a relatively smaller section sized to receive the guidewire.

20. A threader device according to claim 16, wherein:

said threader device includes a locking means integrally molded with at least one of said first and second body members.

* * * * *